United States Patent [19]

Gubelmann et al.

[11] Patent Number: 5,001,280
[45] Date of Patent: Mar. 19, 1991

[54] PREPARATION OF PHENOL BY DIRECT HYDROXYLATION OF BENZENE

[75] Inventors: Michel Gubelmann, Lyons; Philippe-Jean Tirel, Oullins, both of France

[73] Assignee: Rhone-Poulenc Chimie, Courbevoie, France

[21] Appl. No.: 346,216

[22] Filed: May 2, 1989

[30] Foreign Application Priority Data

May 2, 1988 [FR] France ................................ 88 05850

[51] Int. Cl.$^5$ .............................................. C07C 39/00
[52] U.S. Cl. .................................................. 568/716
[58] Field of Search ..................... 568/629, 800, 716

[56] References Cited

U.S. PATENT DOCUMENTS 4,578,521  3/1986  Chang et al. ..................... 568/771

OTHER PUBLICATIONS

Suzuki et al. Chemical Soc. of Japan Chemistry Letters, pp. 953–956 1988.

Primary Examiner—Bruce Gray
Attorney, Agent, or Firm—Burns, Doane Swecker & Mathis

[57] ABSTRACT

Phenol is prepared by directly hydroxylating benzene with nitrous oxide, preferably in vapor phase, on a substrate of acidified zeolite particulates, advantageously ZSM-5 zeolite particulates, and such acidified zeolite particulates having a molar ratio $SiO_2/Al_2O_3$ of greater than about 90, preferably up to 500.

10 Claims, No Drawings

PREPARATION OF PHENOL BY DIRECT HYDROXYLATION OF BENZENE

CROSS-REFERENCE TO COMPANION APPLICATION

Our copending application, Ser. No. 346,215, now U.S. Pat. No. 4,982,013, filed concurrently herewith and assigned to the assignee hereof.

BACKGROUND OF THE INVENTION

1. Field of the Invention

The present invention relates to the preparation of phenol and, more especially, to the preparation of phenol by direct hydroxylation of benzene.

2. Description of the Prior Art

Various processes for the synthesis of phenol, in particular from benzene, have long been known to this art (Kirk-Othmer/Thurman C., vol. 17, pp. 373–384).

For example, benzene is contacted with propylene in the presence of a Lewis acid, such as aluminium trichloride, or in a heterogeneous medium in the presence of a phosphated silica.

The cumene produced is oxidized in a second step to cumene hydroperoxide which in turn is converted to phenol in a sulfuric medium. This technique is still employed today, but requires three stages and involves peroxide intermediates which the industry would prefer to avoid.

Those skilled in this art have long sought, essentially unsuccessfully, to introduce the desired hydroxyl group directly onto the benzene nucleus. The only publication describing the direct introduction of a hydroxyl group onto a benzene nucleus is believed to be the paper by Iwamoto, published in the Journal of Physical Chemistry, 87, 6 (1983).

Such benzene hydroxylation reaction is carried out by means of nitrous oxide ($N_2O$) in the presence of a catalyst based on an oxide of a metal of Groups V or VI of the Periodic Table.

Vanadium oxide is the preferred oxide among the oxides of the metals of Groups V and VI of the Periodic Table. It is more preferred to employ such oxide deposited onto a support based on silica, in an amount by weight ranging from 1% to 10% relative to the support. The support preferably is composed of silica, since alumina in most cases causes the formation of a mixture of carbon oxides.

This particular process was of interest, but the requirement for special catalysts made it relatively unattractive to industry.

Thus, serious need continues to exist in this art for a process for the direct hydroxylation of the benzene nucleus on a simple and readily available substrate.

SUMMARY OF THE INVENTION

Accordingly, a major object of the present invention is the provision of an improved process for the preparation of phenol by the direct hydroxylation of benzene.

Briefly, the present invention features the preparation of phenol by contacting benzene with nitrous oxide on an acidified zeolite.

DETAILED DESCRIPTION OF THE PREFERRED EMBODIMENTS OF THE INVENTION

More particularly according to the present invention, exemplary of the zeolite substrate are the commercial forms thereof, such as:

(i) zeolite ZSM-5 (marketed by Mobil), the preparation of which is described in U.S. Pat. No. 3,702,886;

(ii) zeolite US-Y (marketed by Toyo-Soda);

(iii) zeolite HY (marketed by Union Carbide), under reference LZY 82; and (iv) zeolite H-mordenite (marketed by La Grande Paroisse).

It is preferred to use the commercial zeolite ZSM-5.

The zeolite has an $SiO_2/Al_2O_3$ ratio greater than 90, preferably ranging from 90 to 500.

According to the present invention, the commercial zeolite is preferably acidified by addition thereto of an inorganic acid selected from among hydrochloric acid, sulfuric acid, nitric acid, perchloric acid and phosphoric acid, or an organic acid selected from among halosulfonic, halomethanesulfonic and halocarboxylic acids, and preferably trifluoromethanesulfonic acid.

The organic acids offer no advantage vis-a-vis the inorganic acids Moreover, they are also more costly.

In a preferred embodiment of the invention, the zeolite is acidified by soaking it in a volume of acid, having a normality of from 0.1N to 2N, in an amount of from 10 ml/g to 100 ml/g, per gram of zeolite. Such soaking may be carried out in a single step or, preferably, in several successive steps.

The nitrous oxide is employed pure, or in admixture with an inert gas which does not contain oxygen, such as nitrogen.

The benzene is preferably introduced in admixture with nitrous oxide, in a molar or volume ratio of nitrous oxide relative to benzene ranging from 1 to 10.

In another preferred embodiment of the invention, the benzene is vaporized, is next mixed with the nitrous oxide in the proportions given above, and is then circulated over the zeolite. The reaction preferably is carried out at a temperature of from 300° to 500° C.

The reaction gases containing the phenol are lastly condensed.

In order to further illustrate the present invention and the advantages thereof, the following specific examples are given, it being understood that same are intended only as illustrative and in nowise limitative.

In said examples to follow, the following abbreviations were used:

DC = degree of conversion = product converted/product introduced, in moles;

CY = yield of converted product = desired product/converted product, in moles.

EXAMPLE 1

Preparation of the catalyst 10 g of commercial zeolite NaZSM5 were contacted with 100 ml of a 1N HCl solution at 60° C. for 4 hours under stirring. The treated zeolite particulates were permitted to cool and were washed with demineralized water. The solids were filtered off and dried in an oven at 100° C.

The washing operation described above was repeated 8 times. The dried product obtained after the 8th washing was ground.

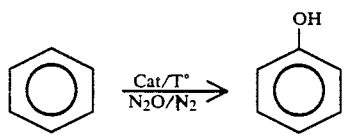

| EXPERIMENTAL CONDITIONS: | |
|---|---|
| Vapor phase | continuous |
| Catalyst | HZSM-5 |
| | pore diameter: 550 ppm |
| | $SiO_2/Al_2O_3$ ratio = 120 |
| Temperature | test 400° C. |
| Contact time | 1 second |
| Molar ratios | Benzene/$N_2$/$N_2O$ |
| | 2/5/8 |

The degree of conversion of benzene was 16%.

The selectivity to phenol was greater than 95% (determined: 98%.)

Control Test (a)

The procedure of Example 1 was repeated, except that the HZSM-5 catalyst had an $SiO_2/Al_2O_3$ ratio of only 50.

The results obtained, all other conditions remaining the same, were the following:

DC=1.9%
CY>95%

EXAMPLE 2

The procedure of Example 1 was repeated, except that the catalyst was a zeolite HNaZS-5 which had an $SiO_2/Al_2O_3$ ratio of 120.

The results obtained, all other conditions remaining the same, were the following:

DC=9.5%
CY>95%

Control Test (b)

The procedure of Example 1 was repeated, except that the catalyst was the commercial zeolite NaZSM-5 which had an $SiO_2/Al_2O_3$ ratio of 120, untreated.

The results obtained, all other conditions remaining the same, were the following:

DC=0

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of phenol, comprising directly hydroxylating benzene with nitrous oxide on a substrate of acidified zeolite particulates having a molar ratio $SiO_2/Al_2O_3$ greater than about 90.

2. The process as defined by claim 1, said acidified zeolite particulates comprising a HZSM-5 zeolite, an HY zeolite or H-mordenite zeolite having a molar ratio $SiO_2/Al_2O_3$ ranging from 90 to 500.

3. The process as defined by claim 2, said acidified zeolite particulates comprising a ZSM-5 zeolite.

4. The process as defined by claim 1, said zeolite particulates having been acidified with an inorganic acid.

5. The process as defined by claim 4, said inorganic acid comprising hydrochloric acid, sulfuric acid, nitric acid, perchloric acid, or phosphoric acid.

6. The process as defined by claim 1, wherein the molar ratio of nitrous oxide to benzene ranges from 1 to 10.

7. The process as defined by claim 1, wherein said nitrous oxide is admixed with an inert gas.

8. The process as defined by claim 7, said inert gas comprising nitrogen.

9. The process as defined by claim 1, comprising vaporizing the benzene, admixing it with the nitrous oxide, and contacting the admixture with the acidified zeolite particulates.

10. The process as defined by claim 1, carried out at a temperature ranging from 300° to 500° C.

* * * * *